United States Patent
Tao et al.

(10) Patent No.: US 6,649,808 B1
(45) Date of Patent: Nov. 18, 2003

(54) DISPOSABLE ABSORBENT ARTICLES COMPRISING MICROPOROUS POLYMER FILMS WITH REGISTERED GRAPHICS

(75) Inventors: Jie Tao, Ashiya (JP); Ebrahim Rezai, Kobe (JP)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/555,937

(22) PCT Filed: Dec. 19, 1997

(86) PCT No.: PCT/US97/23613

§ 371 (c)(1),
(2), (4) Date: Jun. 6, 2000

(87) PCT Pub. No.: WO99/32164

PCT Pub. Date: Jul. 1, 1999

(51) Int. Cl.[7] .................................................. A61F 13/15
(52) U.S. Cl. ...................................................... 604/370
(58) Field of Search .................................. 604/367, 370, 604/375, 361

(56) References Cited

U.S. PATENT DOCUMENTS

| 4,923,650 A | | 5/1990 | Antoon, Jr. et al. | |
|---|---|---|---|---|
| 5,289,093 A | * | 2/1994 | Jobard | 318/434 |
| 5,364,381 A | * | 11/1994 | Soga et al. | 604/358 |
| 5,454,801 A | * | 10/1995 | Lauritzen | 604/378 |
| 5,458,590 A | * | 10/1995 | Schleinz et al. | 101/483 |
| 5,695,868 A | * | 12/1997 | McCormack | 428/516 |
| 5,837,352 A | * | 11/1998 | English et al. | 128/849 |
| 6,075,178 A | * | 6/2000 | La Wilhelm et al. | 604/358 |
| 6,096,014 A | * | 8/2000 | Haffner et al. | 604/367 |

FOREIGN PATENT DOCUMENTS

| EP | 0 352 802 A2 | 1/1990 | C08J/5/18 |
|---|---|---|---|
| GB | 2 210 375 A | 6/1989 | C08K/3/10 |
| WO | WO 94/04606 | 3/1994 | C08K/3/00 |
| WO | WO 95/26208 | 10/1995 | A61L/15/24 |

* cited by examiner

Primary Examiner—Weilun Lo
Assistant Examiner—Catherine L Anderson
(74) Attorney, Agent, or Firm—Jack L. Oney, Jr.; Jeffrey R. Moore; Ken K. Patel

(57) ABSTRACT

A disposable absorbent article is disclosed, comprising a topsheet, a backsheet and an absorbent layer between the topsheet and the backsheet, wherein the backsheet is comprised of a microporous polymer film printed with a registered graphic and comprising by weight: from about 30% to about 60% of a polyolefin; and from about 40% to about 80% of calcium carbonate; wherein the film has a "b" value of between about 0 and about 0.5 and exhibits less than about 2% thermal shrinkage at about 50° C. and about 50% relative humidity for one week.

2 Claims, 4 Drawing Sheets

DISPOSABLE ABSORBENT ARTICLES COMPRISING MICROPOROUS POLYMER FILMS WITH REGISTERED GRAPHICS

FIELD

The present invention relates to disposable absorbent articles comprising microporous polymer films. More specifically, the present invention relates to disposable absorbent articles comprising microporous polymer films that are particularly suitable for the printing of registered graphics thereon.

BACKGROUND

Polymeric materials provided in the form of films or sheets have been used in a variety of commercial products, including diapers, feminine care products, adult incontinence products, and the like. In the manufacture of disposable absorbent articles, such as diapers, microporous polymer films have generally been incorporated into the structure of the article as a part of the layers that are positioned away from the wearer's body during use (often called "the backsheet"). The backsheet provides a liquid impervious barrier so that exudates absorbed and contained in the absorbent core of the article are prevented from leaking, and particularly so that urine stains outside the diaper are prevented.

A nonwoven material is often laminated or otherwise adhered to a microporous polymer film to form the backsheet of a disposable article. The nonwoven material provides the appearance of cloth and a cloth-like feel on the outside of the garment such that wearers and caregivers perceive a garment-like comfort. The combination of a nonwoven material and a microporous film is suitable for disposable absorbent articles such as diapers, including pull-on type and tape-type diapers, feminine care products, and adult incontinence products. An exemplary pull-on type disposable diaper, which is put on by inserting the wearer's legs into the leg openings and sliding the garment up into position about the lower torso, is disclosed in Buell U.S. Pat. No. 5,569,234, "Disposable Pull-on Pant".

For disposable absorbent articles, especially disposable diapers, it is also often desired to provide graphic designs on the articles to enhance their appearance and their consumer acceptance. In previously known articles, the nonwoven layers have typically been printed with such graphic designs. This is because the printing process for nonwoven materials is typically easy to control, because the surfaces of such materials tend to provide stronger mechanical, properties that make them more amenable to printing. See, e.g., EP Publication No. 0 604 729; Yeo U.S. Pat. No. 5,503,076; Schleinz U.S. Pat. No. 5,458,590. However, high resolution, multi-color registered graphics, which are consumer-preferred, usually cannot be printed on such materials. Thus the quality of the graphics that can be printed upon nonwoven materials is typically much lower than that which can be achieved by printing upon microporous film.

Microporous polymer films provide excellent surface characteristics that make them suitable for the printing of high resolution graphics. However, the existing microporous polymer films, see, e.g., Japanese Laid-Open Patent App. (Kokai) No. 9-25372, are not mechanically stable enough to support the printing of the high resolution, multi-color registered graphics that are consumer-preferred. This is due in large part to their thermal instability. The thermal shrinkage associated with existing microporous materials has made it difficult to exploit their ability to support the application of high resolution graphics.

It has also been found that a high degree of whiteness, i.e., the visual appearance of the white color of the article as seen by the consumer, is very important to the consumer. Consumers tend not to accept articles that incorporate films having a yellowish or off-white shade. In addition, breathability, the ability of the article to allow water vapor to escape, is important for wearer comfort and for consumer skincare acceptance. A lack of breathability may result in a hot, stuffy, skin-unfriendly product for the wearer.

Based on the foregoing, there is a need for disposable absorbent articles comprising a microporous polymer film that is mechanically stable enough to support the printing of high resolution, multi-color registered graphics, while also providing breathability and a high degree of whiteness. None of the existing absorbent articles provides all of the advantages and benefits of the present invention.

SUMMARY

The present invention is directed to a disposable absorbent article comprising a topsheet, a backsheet and an absorbent layer between the topsheet and the backsheet, wherein the backsheet is comprised of a microporous polymer film printed with a registered graphic and comprising by weight: from about 30% to about 60% of a polyolefin; and from about 40% to about 80% of calcium carbonate; wherein the film has a "b" value between about 0 and about 0.5 and exhibits less than about 2% thermal shrinkage at about 50° C. and about 50% relative humidity for one week.

These and other features, aspects, and advantages of the invention will become evident to those skilled in the art from a reading of the present disclosure.

BRIEF DESCRIPTION OF THE DRAWINGS

While the specification concludes with claims particularly pointing out and distinctly claiming the invention, it is believed that the present invention will be better understood from the following description of preferred embodiments taken in conjunction with the accompanying drawings in which:

DETAILED DESCRIPTION

All references cited herein are incorporated herein by reference in their entireties. Citation of any reference is not an admission regarding any determination as to its availability as prior art to the claimed invention.

All percentages herein are by weight of compositions unless specifically stated otherwise. All ratios are weight ratios unless specifically stated otherwise. As used herein, the term "comprising" means that other steps and other ingredients which do not affect the end result can be added. This term encompasses the terms "consisting" of and "consisting essentially of".

The microporous polymer films that are preferred for use in the dsisposable absorbent articles of the present invention are formed from a mixture of a polyolefin, usually supplied as a resin, and calcium carbonate ($CaCO_3$) particles. Exemplary polyolefins preferred for use herein include polyethylene and polypropylene. Because polyethylene has a lower modulus and a lower melting point than polypropylene, it is generally easier to process than polypropylene. For this reason, polyethylene is more preferred. Alternatively, other thermoplastic polymers may be used for the films of the present invention. Preferably, from about 30% to about 60% of a polyolefin is used in the films of the present invention; more preferably, from about 45% to about 55% of polyethylene.

The $CaCO_3$ is used to provide microporosity, as described more fully below. However, it may tend to impart a slight yellow shade to the film. It is believed that any such yellow shade is highly unacceptable to consumers, who tend to prefer a bright, intense white appearance. A bright white appearance can be achieved by selecting a grade of $CaCO_3$ that has a very white color. A bright white appearance can also be achieved by adding a small amount of titanium dioxide ($TiO_2$) to the polyolefin and $CaCO_3$ during the mixing stage of the film formation process, if the grade of $CaCO_3$ used is not white enough to provide the finished film with the desired whiteness. In such a case, the addition of the $TiO_2$ counteracts the yellowing effect of the $CaCO_3$.

$TiO_2$ is generally whiter than $CaCO_3$, but it is also generally more expensive and more difficult to blend during extrusion. If $TiO_2$ is added, preferably it should be added in an amount less than about 5 wt %, since amounts greater than about 5 wt % may be difficult to process.

Figure 1:
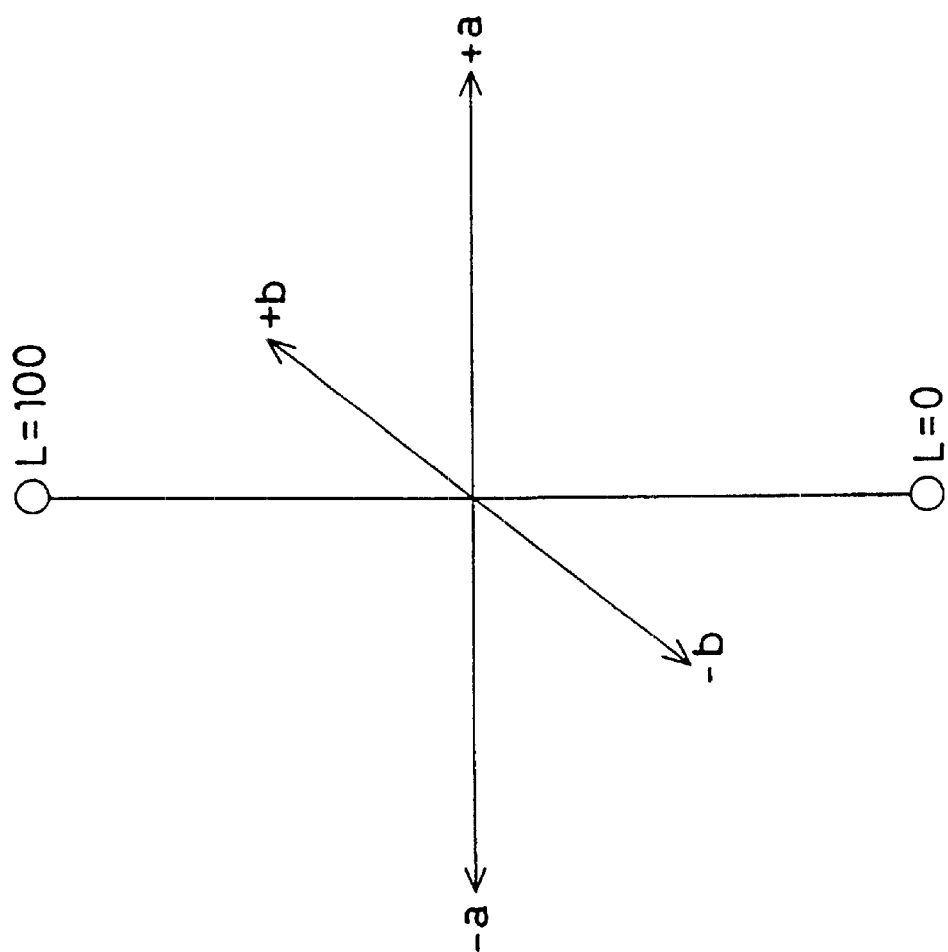
FIG. 1 is a representation of a coordinate system for colorometric measurement.

"Whiteness" as used herein generally refers to the absence of yellow. The whiteness of the microporous films herein may be measured using the Color Model of the ColorQUEST 45/0 instrumentation available from HunterLab, 11491 Sunset Hills Road, Reston, Va. 22090 USA. See also, *The Measurement of Appearance*, Hunter, Richard S., Hunter Associates Laboratories, 9529 Lee Highway, Fairfax, Va. 22030 USA. The Color Model describes the color of any material on the basis of three parameters: L, a, and b. The Color Model may be graphically represented by the coordinate system shown in FIG. 1. Referring to FIG. 1, in the coordinate system shown, "L" is a measure of the lightness of a sample, ranging from L=0 (blackness) to L=100 (whiteness). The quantities "a" and "b" are called opponent-type coordinates. They indicate the degree of redness (positive "a" values), greenness (negative "a" values); and the degree of yellowness (positive "b" values), blueness (negative "b" values). For neutral colors (e.g., white, gray, black), "a" and "b" should be about zero. The higher the values of "a" and "b" for a given sample, the more saturated or chromatic is the color of that sample.

The most important parameter for the films of the present invention is the "b" value, due to the lack of consumer acceptance of yellowish films. Using the ColorQUEST instrument under the conditions of the 10°/D65 international standard and a 10° reflecting angle, the "b" value for the films of the present invention is preferably between about 0 and about 0.5, more preferably as close to zero as possible.

In addition to the polyethylene and the $CaCO_3$, small amounts of other additives, such as antioxidants or lubricants, may also be added during the initial mixing stage of the film formation process. These other additives should preferably be added in the range of about 0.01 wt % to about 0.05 wt %.

"Microporosity" refers to the functional property of the film that permits an article such as a diaper to deliver improved skin health, because the microporous holes permit moisture vapor transmission between the inside of the diaper, i.e., the wearer's skin, and the outside of the diaper. Good moisture vapor transmission, or "breathability", also increases the wearer's comfort by providing a less stuffy feeling. The microporous holes in the films of the present invention are formed generally concentrically around the particles of $CaCO_3$ during the drawing stage of the film formation, as described more fully below. The microporous holes form on the surfaces of the film as well as throughout the thickness of the film, with the size of the microporous holes being related to the size of the $CaCO_3$ particles. In general, the size of the holes surrounding the particles is directly related to the size of the particle. Thus, small particles will cause the formation of small holes, while large particles will create large holes. However, limiting the size of the microporous holes is also important, because even though larger holes result in greater breathability, they also increase the risk of leakage.

The size of the holes may also be affected by the drawing ratio during the drawing step of the film manufacture. Preferably, to achieve optimal breathability, small sized $CaCO_3$ particles are used and the drawing ratio is about 2–3 times.

Moisture vapor transport rate ("MVTR") is a characteristic measure of breathability and "microclimate" inside the diaper. MVTR refers to the permissible moisture volume from one side of the film to the other side of the film per area unit (e.g., per square meter) and per time unit (e.g., per one day). High MVTR is desirable for good skincare because the air can be well ventilated between the inside and the outside of the diaper. However, if the MVTR is too high, the risk of odor, noticeable moisture leakage, or both is present. The control of MVTR is therefore important in applications involving microporous film technology.

The MVTR of a breathable film may be measured by the Cup Test method. This method is described as follows. A known amount of calcium chloride ($CaCl_2$) is put into a stainless steel container. The $CaCl_2$ with water level measurement useful herein may be purchased from Wako Pure Chemical Co., Ltd. A film sample is placed on the top of the container, and the container is tightly closed with a cap and screws. The cap has a hole through it and thus moisture outside the container can diffuse into the container through the film. The container with the film test sample is then placed in a constant temperature and humidity environment for a fixed period of time. The amount of moisture absorbed by the $CaCl_2$ in the container is a measure of the moisture permeability of the film.

Using the Cup Test method wherein the stainless steel container is a cylindrical container with a diameter of 30 mm and a depth of 50 mm, with constant environment conditions of 75% relative humidity and 40° C., the films of the present invention preferably have an MVTR of at least about 3200 grams/m$^2$ per day, with about 3700 grams/m$^2$ per day being more preferable for diapers. Preferably, the MVTR is as high as possible with no leaks.

The microporous polymer films of the present invention are preferably formed according to the following process. The polyolefin polymer, preferably from about 30% to about 60% and more preferably from about 35% to about 55% of polyethylene, and the $CaCO_3$, preferably from about 40% to about 80% and more preferably from about 45% to about 65% are mixed at a high temperature, preferably greater than the melting point temperature of the polymer. For example, if polyethylene is used, the mixing temperature should be in the range of about 120° C. to about 130° C. If $TiO_2$, and any other additives are to be included in the film, they should also be added to this initial raw material mixture at the outset of the process. If $TiO_2$ is to be added, it is preferably added at a level of less than about 5%.

After mixing, the mixture is fed through pullers and then pumped to an extruder. After extrusion, the mixture is cast as a thin film. Generally, the casting temperature is also greater than the melting point temperature of the raw material polyolefin polymer.

After casting, the film is drawn, while remaining at a temperature higher than ambient. The drawing step is the point at which the microporous holes form around the particles of $CaCO_3$. Drawing rolls are preferably used for the drawing step. The velocity of each drawing roll should basically be greater than that of the drawing roll preceding it. Thus, the velocity of the second drawing roll is greater than the velocity of the first drawing roll, with the first drawing roll having the lowest velocity of all the drawing rolls.

The drawing step locks in residual strain. After the film has been drawn, it is not thermally stable due to the energies existing between the molecules of the film. Thus, in order to achieve the thermal stability necessary to support the printing of high resolution graphics on the film, further processing is necessary.

The film in the drawn state is then annealed. It is believed that the annealing step eliminates the stresses between the micromolecules of which the film is comprised, and thus it is critical for providing the film with thermal stability. The annealing step provides the stress relief that would otherwise occur under storage and transport conditions at temperatures elevated above about the glass transition temperature $T_g$ of the polyethylene (or other polymer) used. In other words, if annealing is not carried out as described herein, this stress relief will occur when the finished product that incorporates the film, e.g., a diaper, experiences the elevated temperatures associated with storage and transport. At that time, the stress will release, which generally distorts the appearance of both the product itself and especially the appearance of the registered graphics, and which may effect the overall quality of the film integrity.

However, if the annealing conditions are too strict, for example if the either the annealing temperature is too high, the annealing time is too long, or both, many of the microporous holes will shrink at high tension, thereby decreasing breathability of the film.

After annealing, the film is preferably subjected to a corona treatment in which it is placed in a sealed environment at about ambient temperature. $O_3$ ions are radiated throughout the environment. It is believed that the corona treatment increases the dyne level for the printing side of the film, i.e., the side upon which the graphics are to be printed. High dyne levels indicate that each area of the printing ink will require less surface area on the film for adhesion; thus, the higher the dyne level, the higher and better the graphic resolution can be made. Films of the present invention preferably have a dyne level of greater than about 35 and more preferably greater than about 40.

Figure 2:
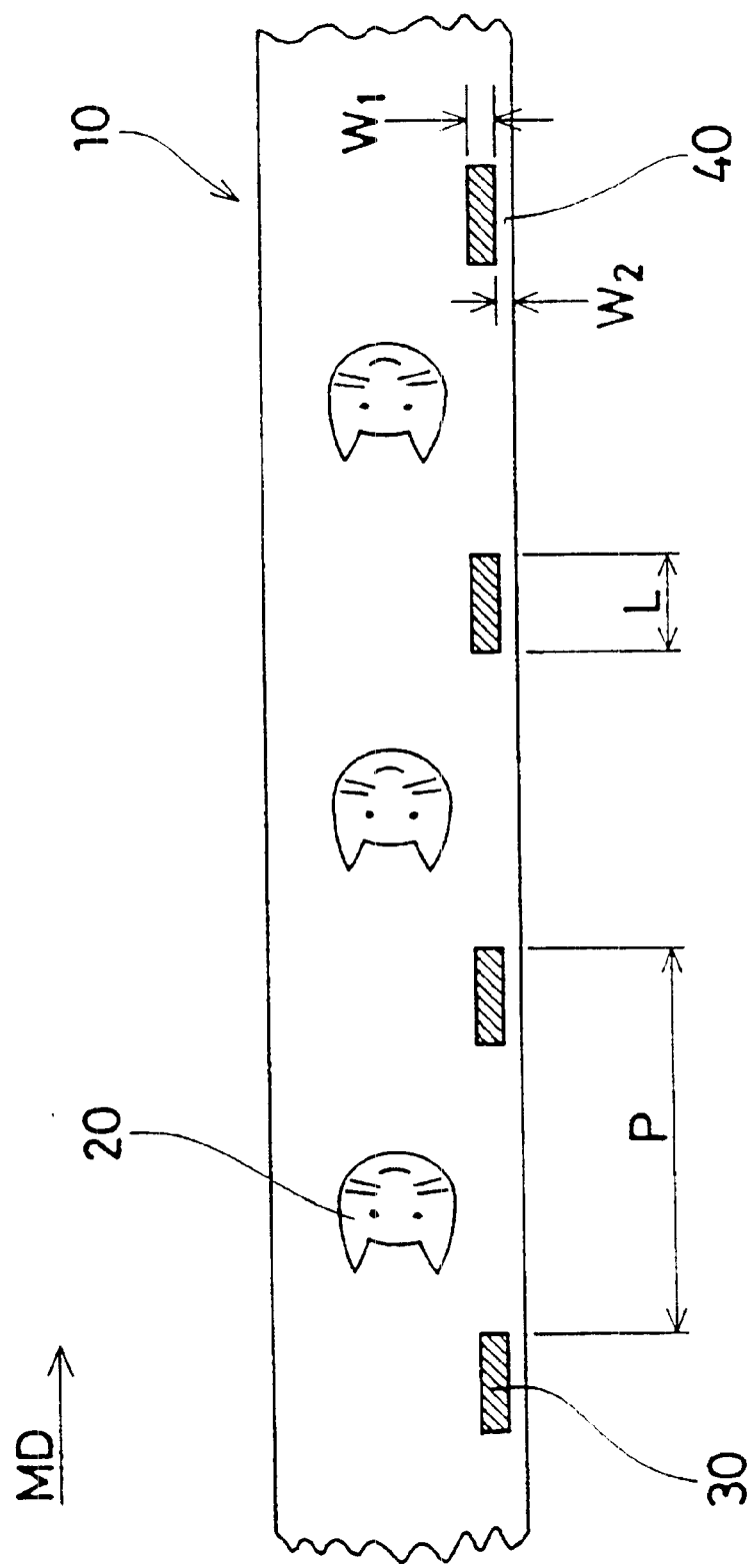
FIG. 2 is a partial top view of a preferred embodiment of the film of the present invention printed with registered graphics.

After the corona treatment, the finished film can be rolled up or packaged in preparation for printing the registered graphics on the film, for example as shown in FIG. 2. Printing techniques useful herein for providing multi-color registered graphics include flexographic printing process and gravure printing process, with flexographic printing being preferred.

An exemplary portion of a film of the present invention is shown in FIG. 2. The film 10 is shown printed with the registered graphics 20 separated by pitch length P. It will be well understood by those of skill in the art that the graphics 20 may be of any shape, design, color or size, and that single or multiple designs may be used. Alternatively, pre-bonded, pre-applied, pre-cut, or pre-glued objects may be used. Timing marks 30 having a width W1 and a length L are also shown. Timing marks 30 are, used so that the optical sensors of the combining and cutting mechanisms can detect the marks and thereby to properly align and to 25 trim the film or film/nonwoven backsheet combination. Preferably, the timing marks are sized and placed such that they are removed when the film is trimmed, so that they are not a part of the finished product and thus not visible to the consumer. Alternatively, it may be part of the finished product but invisible to the consumer, while still being detectable by the machinery.

The distance between the timing mark and the edge of the film is referred to as a shadow mark. The shadow marks 40 are shown as having width W2 in FIG. 2. For a disposable diaper manufacturing line, pitch length P of from about 475 mm to about 485 mm, width of timing mark W1 of from about 7 mm to about 10 mm, length of timing mark L from about 20 mm to 25 mm, shadow mark width W2 from about 0 to about 10 mm, and red color of timing mark for contrast are exemplary parameters for the timing marks.

As noted above, the films of the present invention exhibit high thermal stability as a result of the raw materials selection and the processing conditions, particularly the drawing and annealing steps. After the film has been formed and during the time in which it is subsequently stored, often in a warehouse where it is exposed to elevated temperatures after production, the film material tends to shrink. This shrinkage is a function of the time, temperature and humidity conditions of storage and transport, parameters that cannot readily be controlled. For example, during one week at 50° C., shrinkage levels of up to 5–10% have been observed for certain conventional films. Different levels of shrinkage can even vary within the same roll of film depending upon the level of tension that was used to wind the roll. This thermal instability has typically made it difficult to incorporate such films into consumer products in a phased relationship.

The thermal shrinkage rate of microporous films may be measured under the following conditions. Film samples are cut as 500 mm long in the machine direction and 150 mm wide in the cross direction. As used herein, "machine direction" means the direction of movement along a manufacturing line, and "cross direction" means the direction substantially perpendicular to the machine direction. The machine direction is represented by the arrow labeled MD in FIG. 2. Two straight lines are drawn as 250 mm in the machine direction and 100 mm in the cross direction. The film samples are placed into an oven controlled at 50° C. and 50% relative humidity for one week. The shrunken lengths of the lines are calculated as the thermal shrinkage rate, based upon the original lengths.

Under the test conditions described above, the films of the present invention typically experience only from about 0% to about 5% shrinkage in the machine direction, more preferably less than about 2%. In the cross direction, the films typically experience negligible shrinkage. Thus, the films of the present invention provide both the good surface characteristics of microporous polymer films that readily support high-resolution printed graphics while being susceptible to only negligible degrees of thermal shrinkage.

The films of the present invention also preferably have other desirable properties that are beneficial in the processing of the film in connection with the manufacture of absorbent articles. Although it will be understood by those of skill in the art that the films of the present invention have many uses, for purposes of illustration the following description will focus upon use of the film as a backsheet for a disposable diaper.

Web modulus is important to the stable operation of a registered graphics phasing system. As used herein, "web modulus" means the mechanical property defined as the slope of a material's stress/strain curve. While the absolute value of the web modulus is not as important as its standard deviation within a roll of film, the modulus determines the amount of tension required to force an adjustment in the phase position of the film during processing. Films having a web modulus in the range of about 4000 g/in to about 13,000 g/in have been found to be preferred for the printing of high resolution graphics upon films useful as diaper backsheets.

Film caliper control is important to the winding of a roll of backsheet film and to its processability. The term "film caliper" refers to the thickness of the film. During the film making process, various localized levels of film shrinkage sometimes occur in the case of microporous films. A wide variation in film caliper may cause wrinkles or an uneven surface or both in a roll of film. During processing, caliper variations may cause film deformation, film breakage at the thinner areas, and line stoppage due to problems caused by tension control problems. Exemplary ranges for film calipers herein are in the range of about 0.022 mm to about 0.038 mm, with caliper variation of ±6.3%.

Thermal enthalpy ($\Delta H$) is another important characteristic in providing heat resistance to the polymer film, especially during processes such as hot-melt glue lamination that may be part of a diaper manufacturing line. A high enthalpy characteristic can provide a broad range for adhesive temperature adjustment because the film materials have strong heat-resistance. As enthalpy increases, however, the stiffness of the microporous film material also increases, leading to possible issues with comfort and other manufacturing processes that depend on heat response of the film. Without being bound by theory, it is believed that the link between added stiffness and rising enthalpy is due to rising forces between macromolecules.

Basis weight refers to the weight of one square meter of planar web material. Exemplary basis weights herein are between about 20 grams per square meter (gsm) and about 40 gsm for films useful as a diaper backsheet.

Other film parameters that impact the printing process, the diaper manufacturing process, or both, include film width, length of the film roll, core diameter of the film roll, splices, timing marks, and printing orientation.

Printing orientation refers to the direction of travel of the graphic-printed film through the manufacturing line. For a disposable diaper manufacturing line, it has been found useful for the printed side of the microporous polymer film to be wound inside the roll, with the area that will become the front of the product leading first off of the roll, with the timing mark orientation on the left and the timing shadow mark on the right.

Figure 3:
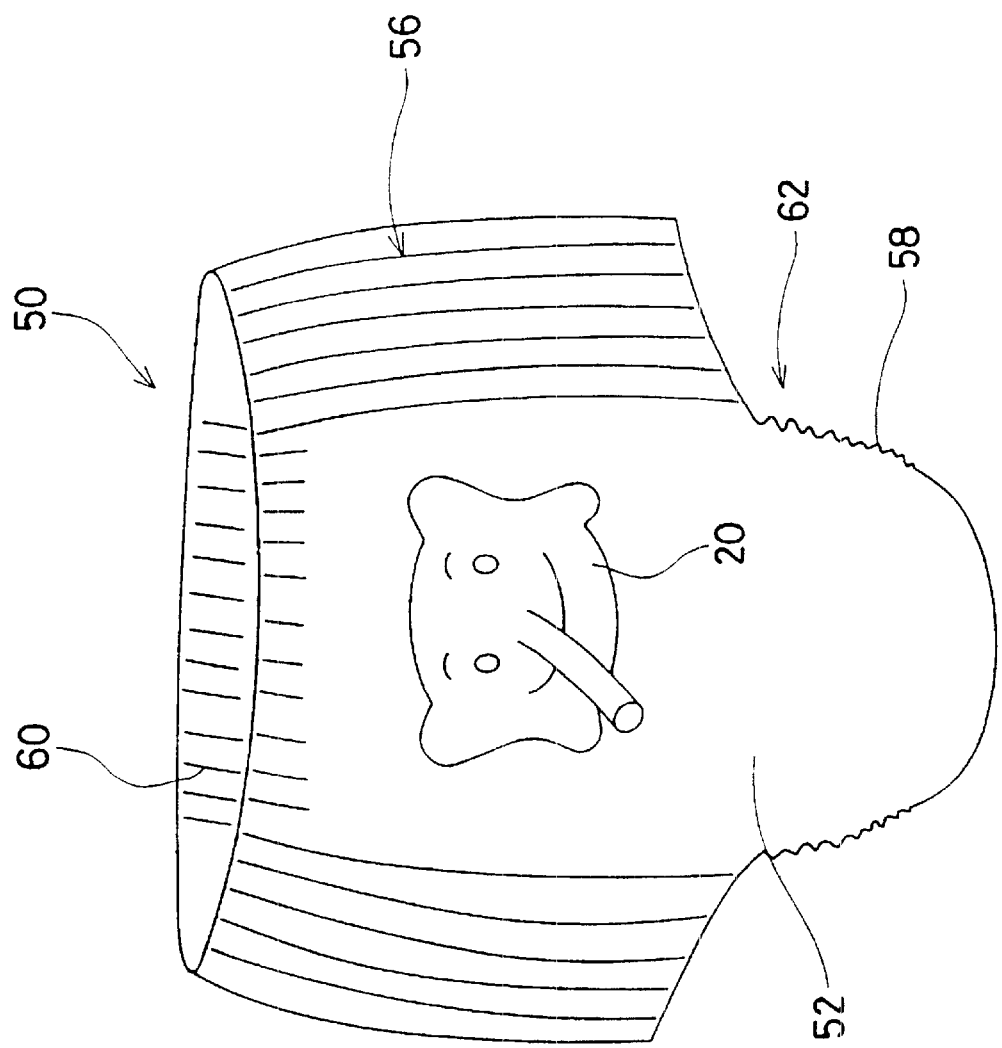
FIG. 3 is a front view of a preferred embodiment of a disposable absorbent article having registered graphics.

Referring to FIG. 3, there is shown a preferred embodiment of a disposable pull-on diaper 50, which is generally pulled onto the body of the wearer by inserting the legs into the leg openings 62 and pulling the article up over the waist. Generally, "pull-on diaper" refers to pull-on garments worn by small children and other incontinent individuals to absorb and contain body exudates. It should be understood that other pull-on garments such as training pants, incontinent briefs, feminine briefs, feminine hygiene garments or panties, and like, are included herein. It should further be understood that tape-type diapers are included herein.

Figure 4:
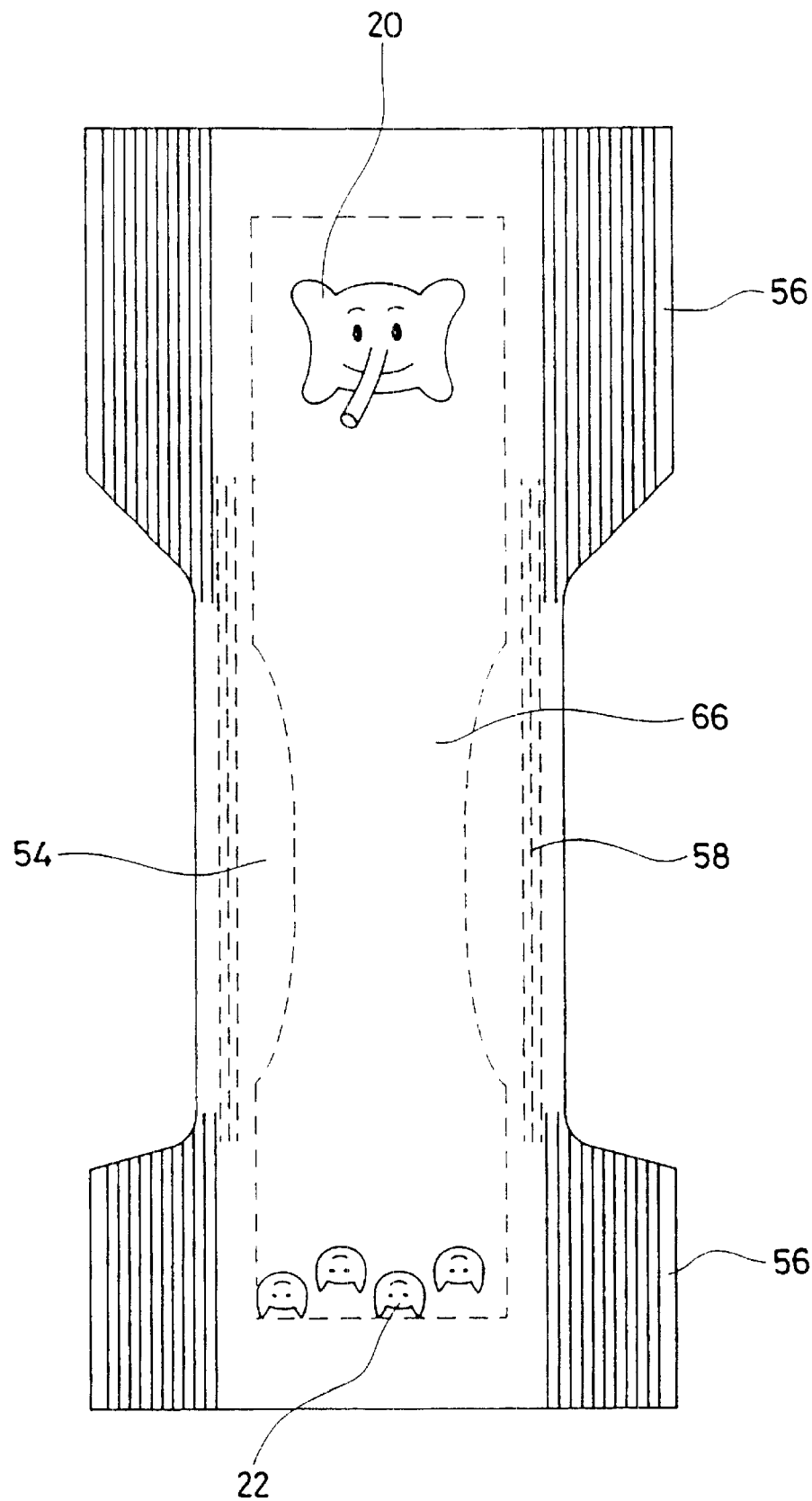
FIG. 4 is a simplified plan view of another preferred embodiment of a disposable absorbent article having registered graphics.

Referring to FIGS. 3 and 4, the diaper 50 is generally comprised of a backsheet 52, a topsheet 54 and an absorbent layer 66 (shown in dashed lines in FIG. 4) located between the backsheet 52 and the topsheet 54. The topsheet 54 is located to be placed facing the body or nearest the body when the diaper is worn and is generally provided with a liquid permeable region so that body exudates can flow through the topsheet 54 to the absorbent layer 66. The backsheet 52, which is placed away from the body during wear, is typically liquid impermeable so that outer clothing or other articles are not wetted by the body exudates. Preferably, the backsheet 52 is comprised of at least a microporous polymer film printed with registered graphics, as described herein. The backsheet 52 may further comprise a layer of nonwoven material laminated to the microporous film layer, in which case there is provided a more cloth-like and garment-like feel than is typically obtained with a film backsheet only.

Elastically extensible side panels 56 are provided to ensure more comfortable and contouring fit by initially conformably fitting the pull-on diaper 50 to the wearer and sustaining this fit throughout the time of wear well past when it has been loaded with exudates. Leg elastics 58 and waist elastic region 60 are also provided to enhance the fit around the legs and waist, respectively.

FIG. 3 shows the front view of the diaper 50 with an exemplary registered graphic 20 positioned in about the upper region of the backsheet, on the front side of the diaper 50. In FIG. 4, there is shown a simplified plan view of an embodiment of a disposable absorbent article in its flat, uncontracted state prior to formation. In this embodiment, registered graphic 20 is shown in the back region of the diaper with graphics 22 additionally shown in the front region.

As will be understood by those of skill in the art, many other features for disposable absorbent articles are within the scope of the present invention. For example, barrier cuffs as described in Lawson and Dragoo U.S. Pat. Nos. 4,695,278 and 4,795,454 are a desirable feature for disposable absorbent articles. In addition, skin care-type topsheets that are provided with lotion thereon for the purpose of reducing skin irritation and chafing are a desirable feature herein.

The aspects and embodiments of the present invention set forth herein have many advantages, including bright white appearance, the capacity to support high resolution, multi-colored registered graphics, and thermal stability.

EXAMPLE

The following example further describes and demonstrates a preferred embodiment of the microporous polymer film for disposable absorbent articles within the scope of the present invention. The example is given solely for the purpose of illustration, and is not to be construed as a limitation of the present invention since many variations thereof are possible without departing from its spirit and scope.

Polyethylene and CaCO₃ are used as the starting materials. The film is cast and drawn in the machine direction. The film has the following properties:

| | |
|---|---|
| Basis weight | 34.3 ± 0.42 gsm |
| Thickness by caliper | 0.042 ± 6.3% mm |
| Heat Shrinkage | |
| MD | 1.4% |
| CD | 0.0% |
| Mechanical Property | |
| MD: | |
| Load at 1% | 114 g/in |
| Load at 3% | 269 g/in |
| Load at 5% | 389 g/in |
| Load at Peak | 1260 g/in |
| Strain at Peak | 188% |
| CD: | |
| Load at Peak | 460 g/in |
| Strain at Peak | 386% |
| MVTR (Cup Test) | 3600 g/m²/24 hr |
| Whiteness | |
| L: white/black | 93.46% |
| a: red/green | −0.24 |
| b: blue/yellow | 0.35 |
| Pitch Size for Registered Marks | 480 ± 4 mm |
| Mark Width | 10 ± 0.2 mm |
| Mark Length | 20 ± 0.5 mm |
| Shadow Mark Width | 0.0 ± 1.0 mm |

The mechanical property of the film refers to tensile strength at a percent strain or at peak, where strains in the range of about 1% to 5% represent strains in the elastic range of the material. After the film has been formed, it can be printed with registered graphics and incorporated into a disposable absorbent article, for example as part of the backsheet of a disposable diaper.

It is understood that the examples and embodiments described herein are for illustrative purposes only and that various modifications or changes in light thereof will be suggested to one skilled in the art without departing from the scope of the present invention.

What is claimed is:

1. A disposable absorbent article comprising a topsheet, a backsheet and an absorbent layer between the topsheet and the backsheet, wherein the backsheet is comprised of a microporous polymer film printed with a registered graphic and comprising by weight:

a. from about 30% to about 60% of a polyolefin; and b. from about 40% to about 80% of calcium carbonate;

wherein the film has a "b" value between about 0 and about 0.5 and exhibits less than about 2% thermal shrinkage at about 50° C. and about 50% relative humidity for one week, wherein the film has a web modulus of from about 4,000 g/in to about 13,000 g/in.

2. A disposable absorbent article comprising a topsheet, a backsheet and an absorbent layer between the topsheet and the backsheet, wherein the backsheet is comprised of a microporous polymer film printed with a registered graphic and comprising by weight:

a. from about 30% to about 60% of a polyolefin; and b. from about 40% to about 80% of calcium carbonate;

wherein the film has a "b" value between about 0 and about 0.5 and exhibits less than about 2% thermal shrinkage at about 50° C. and about 50% relative humidity for one week, wherein the film has a printing side having a dyne level of greater than about 35.

* * * * *

UNITED STATES PATENT AND TRADEMARK OFFICE
CERTIFICATE OF CORRECTION

PATENT NO. : 6,649,808 B1
DATED : November 18, 2003
INVENTOR(S) : Tao et al.

It is certified that error appears in the above-identified patent and that said Letters Patent is hereby corrected as shown below:

Column 1,
Line 50, after the word "mechanical", delete ",".

Column 2,
Line 66, delete ""consisting" of" and insert -- "consisting of" --
Line 67, delete "of"." and insert -- of." --.

Column 6,
Line 11, after the word "are", delete ",".

Signed and Sealed this

Eighth Day of June, 2004

JON W. DUDAS
*Acting Director of the United States Patent and Trademark Office*